United States Patent [19]

Young

[11] Patent Number: 5,059,241

[45] Date of Patent: *Oct. 22, 1991

[54] PLANT GROWTH REGULATION

[75] Inventor: Donald C. Young, Fullerton, Calif.

[73] Assignee: Union Oil Company of California, Los Angeles, Calif.

[*] Notice: The portion of the term of this patent subsequent to Sep. 5, 2006 has been disclaimed.

[21] Appl. No.: 496,365

[22] Filed: Mar. 20, 1990

Related U.S. Application Data

[63] Continuation-in-part of Ser. No. 380,615, Jul. 17, 1989, which is a continuation of Ser. No. 511,161, Jul. 6, 1983, Pat. No. 4,863,506.

[51] Int. Cl.$^5$ .............................................. A01N 37/00
[52] U.S. Cl. ......................................... 71/106; 71/113
[58] Field of Search ................................. 71/106, 113

[56] References Cited

U.S. PATENT DOCUMENTS 3,712,804  1/1973  Müller et al. ........................ 71/113
4,863,506  9/1989  Young .................................... 71/113

FOREIGN PATENT DOCUMENTS 1916054  10/1970  Fed. Rep. of Germany.
51-33068  3/1976  Japan.

OTHER PUBLICATIONS

Tung et al, "Effect of Soil Aliphatic Acids on Young Cane Growth", *Taiwan Tang Yeh Shih Yeh So Yen Chin Hui Poo* No. 41, 45–50, 1966 (CAS 67:89968a).

Tamura et al, "Isolation of L-β-Phenyllactic Acid as a Plant Growth-Regulator Produced by Exobasidium", *Agr. Biol. Chem.* 29(11):1061–2, 1965.

Mikami et al, "Several Synthetic Hydroxy-Acids as Plant Growth Regulators", *Agr. Biol. Chem.* 34(6):977–9, 1970.

Todorova et al., Chemical Abstracts, vol. 93, 68595y (1980).

U.S. Department of Agriculture Miscellaneous Publication No. 654, Woody–Plant Seed Manual, pp. 32–35.

Chemical Abstracts Eighth Collection Subject Index, pp. 17196–17197.

Tung et al., Chemical Abstract, vol. 67, 89968a (1967).
Terent'ev et al., Chemical Abstract 66:54601c (1967).
Smith et al., Chemical Abstract, vol. 73, 426373J (1970).
Radler et al., Chemical Abstract, vol. 74, 50803n (1971).
Hummel, Chemical Abstract, vol. 42, 4097e (1948).
Merck Index (1983) Entry 5174.

*Primary Examiner*—Richard L. Raymond
*Assistant Examiner*—S. Mark Clardy
*Attorney, Agent, or Firm*—Gregory F. Wirzbicki; Michael H. Laird

[57] ABSTRACT

L-(d)-lactic acid, the dextrorotatory isomer of lactic acid, is an effective plant growth regulant which exhibits classical growth regulant activity at very low concentrations and dosage rates. It can be employed to beneficially stimulate the growth of all plant varieties and is particularly useful for stimulating the growth of commercial crops. Thus, L-lactic acid can be employed to stimulate the growth of desired plants and to stimulate the fruit production of fruit-bearing plants. Novel compositions which comprise mixtures of L-(d)-lactic acid and one or more preservatives which are sufficient to prevent the hydrolytic and/or bacterial decomposition of the active isomer are also disclosed.

23 Claims, 1 Drawing Sheet

PLANT GROWTH REGULATION

RELATED APPLICATIONS

This application is a continuation-in-part of co-pending application Ser. No. 07/380,615, filed July 17, 1989 which was a continuation of Ser. No. 06/511,161 filed July 6, 1983, now U.S. Pat. No. 4,863,506.

BACKGROUND OF THE INVENTION

1. Field of the Invention

This invention relates to methods of regulating the growth of plants and, in particular, it relates to methods useful for stimulating the growth and/or fruit production of plants and to compositions useful for regulating plant growth.

2. Description of the Art

Plant growth regulants can be defined as compounds and/or preparations which, in minute amounts, alter the behavior of ornamental and/or crop plants and/or the produce of such plants through physiological (hormonal) rather than physical action. They may either accelerate or retard growth, prolong or break a dormant condition, promote rooting, fruit-set, or increase fruit size or quantity, or affect the growth and/or productivity of plants in other ways. Plant growth regulants are currently classified into one or more of six categories: auxins, gibberellins, cytokinins, ethylene generators, inhibitors, and retardants. Illustrative of known auxins are indole acetic acid, 24-D (2,4-dichlorophenoxyacetic acid), MCPA (4-chloro-2-methyl phenoxyacetic acid), MCPB (4-[(4-chloro-o-tolyl)oxy] butyric acid) which susceptible plants oxidize to MCPA, and BNOA (beta-napthoxyacetic acid). Gibberellins include gibberellic acid and its derivatives, while cytokinins included compositions such as zeatin, kinentin, and benzyl anidene. Presently known ethylene generators include ethylene and Ethephon [(2-chloroethyl) phosphoric acid]. Presently known inhibitors include benezoic acid, gallic acid, and cinnamic acid, while retardants, a recently developed class of plant growth regulants, include compositions which are especially useful in plant height control, particularly in commercial greenhouse-grown floricultural crops.

Lactic acid (alpha-hydroxypropionic acid) is well known and is widely employed in industry as a chemical intermediate. It is usually present in the form of the racemic mixture which is an equimolar mixture of the two possible optical isomers of alpha-hydroxypropionic acid - the levorotatory and dextrorotatory isomers. Levorotatory (l) isomers are isomers of an optically active compound which rotate a beam of polarized light to the left; the dextrorotatory (d) are isomers of the same compound which rotate a beam of polarized light to the right. A second convention employed to define the configurational relationships of dissimilar functional groups bonded to an asymmetric carbon atom, the Fischer method, is based on the geometric arrangement of functional groups relative to each other rather than on the direction (left or right) in which a standard solution of the compound rotates a beam of polarized light. In accordance with the Fischer method, any compound which contains an asymmetric carbon atom of the same configuration as the asymmetric carbon in the arbitrary standard dextrorotatory glyceraldehyde is classified in the D series, while compounds in which the asymmetric carbon atom has the opposite configuration are classified in the L series. Although the Fischer D and L classifications do not correlate with dextro- (d) and levorotatory l optical activity for all compounds, those classifications can be used in combination with the optical activity classifications d and l to define both the geometric arrangement and specific optical activity of any optically active isomer. Thus, the L-isomer of lactic acid, which is dextrorotatory, is defined as L-(d)-lactic acid, and the D isomer is defined as D-(l)-lactic acid. However, both of these characteristics of relatively simple compounds, such as lactic acid, can be adequately defined by reference to only one classification system. L-lactic acid is known to be dextrorotatory, and l-lactic acid is known to have the D configuration according to Fischer. For this reason, the D and L isomers of lactic acid are usually identified only by the D and L designations and without explicit reference to their optical activity. The Fischer classification method is well known in the art and is discussed in more detail in "Introduction to Organic Chemistry", Fieser and Fieser, D. C. Heath and Co., Boston, Mass., (1957) at pages 209-215.

Lactic acid is prevalent in a variety of synthetic and naturally occurring products such as dairy products and fermentation products in which it occurs primarily as the racemic mixture. Specialized fermentation processes can be employed to selectively manufacture either the levorotatory or dextrorotatory isomers. Although some commercially available agricultural products contain fermentation products and lactic acid and are marketed for various applications in the agricultural industry, it has not been observed or suggested that L-(d)-lactic acid is an active plant growth regulant. Furthermore, the lactic acid-containing compositions which are marketed in the agricultural industry usually contain the racemic mixture of both optical isomers in addition to cations such as sodium, potassium, ammonium, etc., and/or other compounds such as surfactants, pesticides, etc., which can react with L-lactic acid and destroy its growth regulant activity.

It also has been suggested that alpha-hydroxy carboxylic acids of higher molecular weight than lactic acid exhibit specific growth regulant activity regardless of the configuration or optical activity of the carboxylic acid employed. U.S. Pat. No. 3,712,804, Mueller et al., discloses that certain alpha-substituted carboxylic acids increase the yield of certain crops by improving the ability of the plant to assimilate water from its environment. The acids have 7 to 10 carbon atoms per molecule and the alpha carbon atom is substituted with one or more functional groups including oxy, hydroxy, amine, and carboxyl groups. The acids are applied to very young plants and the salts and lower alkyl esters and amines have growth regulant activity similar to that of the free acid. The compositions can also contain wetting agents.

The plant growth regulants referred to above and otherwise known in the art, including those discussed in U.S. Pat. No. 3,712,804, all suffer from certain disadvantages that make their use, at least in some applications, less desirable than would be the use of L-lactic acid. Many growth regulant compositions, particularly those which exhibit herbicidal activity at higher dosage rates, are toxic to plants, the environment, and/or animals, including humans. Many are not readily available and are relatively expensive to manufacture as compared to L-lactic acid. Also, many of the known growth regulants, such as the alpha-functional carboxylic acids, salts, esters and amines discussed in U.S. Pat. No. 3,712,804, require plant treatment at a time that may not be opportune for the grower in all instances. Furthermore, many known regulants exhibit a limited spectrum of growth regulant activity, are not useful with many plant varieties, and/or do not adequately regulate crop productivity.

Accordingly, a need exists for improved methods for regulating the growth of plants and for improved compositions useful in such methods. In particular, a need exists for improved methods and compositions for stimulating the desired growth of plants, reducing the toxic effects of such methods and compositions on the environment and animals, including humans, and reducing the expense of so regulating plant growth.

SUMMARY OF THE INVENTION

The invention provides novel methods for regulating the growth of plants and compositions useful in such methods. The methods of this invention involve regulating the growth of plants by contacting the plants with a growth regulating amount of a composition which contains the dextrorotatory L-(d)-isomer of lactic acid. The L-latic acid preferably constitutes at least a major portion of the latic acid present in the applied composition. These methods can be employed either to stimulate the growth and/or fruit production of crop plants and ornamental plants. Contacting the plants with L-lactic acid can be accomplished by applying L-lactic acid directly to the plants or by applying compounds which are water soluble and/or are converted to water soluble compounds in solution or on plant foliage and which generate lactate anion, i.e. lactic acid and salts and esters thereof.

The novel compositions of this invention exhibit plant growth regulant activity and contain a lactic acid generator of which at least a major portion of the lactate anion is the L-(d)-isomer of lactic acid. These compositions also contain a nonreactive preservative such as a sufficient amount of acid to maintain the pH of the composition within the range of about 5 or less and/or a sterilant which is sufficient to inhibit the bacterial decomposition of the lactic acid and/or generator.

The methods of this invention are useful for increasing the growth and/or fruit production of essentially all plant varieties. On fruiting plants, the methods of this invention can be employed to increase both the size and quantity of the fruit produced. These methods also hasten maturity of fruit thereby shortening the crop cycle and they increase the growth rate of agricultural and ornamental grasses, such as alfalfa, rye grass, etc. They can be employed to delay the senescence and thereby extend the fruiting period of annual fruit plants such as tomatoes and corn and to extend the fruiting period of perennials such as citrus, grapes, etc. These methods have the further advantage that they are nontoxic to the environment and to animals, and, at levels employed for stimulating plant growth, the compositions useful in the methods of this invention are nontoxic to the treated plants or to the harvested component of fruiting plants such s food products. Furthermore, the compositions are noncorrosive to storage, transport and application equipment and to animal and vegetable tissue. Thus, they can be easily and safely handled without damage to equipment, personnel, the crop, or the environment. The active component—L-lactic acid—is readily available commercially and is relatively inexpensive, particularly in comparison to various other plant growth regulants which are expensive, sophisticated chemical compounds which require relatively sophisticated processes for their manufacture. Compounds which generate L-lactate anion in aqueous solution, i.e. salts and esters of lactic acid, are also commercially available and can be prepared by known methods of producing salts and esters.

All of the benefits associated with the use of the methods of this invention discussed above also result from the use of the novel compositions of this invention in such methods.

BRIEF DESCRIPTION OF THE DRAWINGS

The methods and compositions of this invention will be better understood by reference to the drawings of which.

DETAILED DESCRIPTION OF THE INVENTION

This invention provides novel methods for regulating the growth of plants and novel growth regulant compositions useful in such methods. The methods involve stimulating the growth of plants by contacting the plants with a composition comprising the dextrorotatory isomer of lactic acid. This can be readily accomplished by applying lactic acid to the plants o by applying to the plants compounds which generate lactic acid/lactate anion in aqueous solution or on plant foliage, such as salts and esters of lactic acid. The novel compositions comprise lactic acid or a lactate anion generator of which at least a major portion is the L-(d)-isomer of lactic acid and a preservative which is nonreactive with the lactic acid and which is sufficient to reduce or prevent the hydrolytic and/or bacterial decomposition of the lactic acid. The methods can be employed to increase vegetative growth and to increase the fruit production of fruit-producing plants. They can also be employed to hasten the maturity of plant fruit, delay and senescence (and thereby extend the fruiting period) of annual plants, and to extend the fruiting period of perennial plants.

The compositions useful in the methods of this invention are broad-spectrum plant growth regulants; thus they can be employed to stimulate the growth and/or fruit-producing capacity of all plant varieties, including fruiting and principally vegetative plants. Fruiting plants, for the purposes of this invention, include plants that bear any variety of produce other than vegetative growth, such as annual and perennial vegetables, fruits, nuts, grains, fiber crops, and the flowering plants. Plants grown primarily for their vegetative productivity (the principal illustration being the wide variety of grasses grown for animal feeds and decorative purposes) can also be treated in accordance with the methods of this invention. Thus, the methods of this invention can be employed to stimulate the growth and fruit-bearing capacity (where relevant) of vegetables, fruits, nuts, grains, grasses, fiber crops, wood crops, and flowering plants.

All varieties of vegetables can be treated in accordance with these methods including lettuce, broccoli, asparagus, onions, tuberous crops such as potatoes, sugar beets and peanuts, tomatoes, beans, etc. Illustrative of fruits that can be treated in accordance with the methods of this invention are peaches, apples, citrus, avocados, cherries, grapes (varietal and table), bananas, etc. Treatable nut crops include walnuts, pecans, almonds, cashews, etc. Essentially all grains can be treated including corn, wheat, sorghum, maize, rice, barley, oats, etc. Illustrative grasses include alfalfa, bermuda, rye, and bluegrass, while illustrative fiber crops include cotton and flax. All wood crops can be stimulated by the methods of this invention including both hardwoods and conifers, such as oak, elm, maple, walnut, spruce, hemlock, alder, loblolly pine, redwood, mahogany, cypress, cedar, Douglas fir, and white pine. Flowering plants which can be treated in accordance with the methods of this invention include all varieties of domestic and commercially grown flowers, such as orchids, roses, chrysanthemums, azaleas, camellias, carnations, pansies, snapdragons, etc.

The compositions useful in the methods of this invention comprise a growth regulating amount of the L-(d)-lactic acid; i.e., the dextrorotatory isomer, or salt or ester thereof. The effectiveness of such compositions to stimulate the growth and/or fruitbearing capacity of vegetation is apparently attributable to the plant growth regulant activity of the uncomplexed, monomolecular, L-(d)-isomer of lactic acid. The D-(l)-isomer of lactic acid not only does not promote vegetative growth or fruit productivity, it appears to inhibit the activity of the L-isomer to the point that the racemic mixture, i.e., the 50—50 blend of the levorotatory and dextrorotatory isomers, has only marginal growth regulant activity, if any. As is the case with all compounds which are applied to plants as solutes, the D-lactic acid does exhibit phytotoxicity if sufficient quantities of that material are applied to the plant. Such activity is very similar to that observed with very simple compounds such as sodium chloride and other soluble salts, which exhibit phytotoxicity when foliarily applied to essentially any crop. At sufficient dosage rates, such compounds will inhibit the growth of plants and will ultimately kill the treated plants.

I have also found that L-lactic anhydride and polylactides of the L-isomer (self esterification products of lactic acid) are active plant growth regulants and are as active as monomolecular L-lactic acid. All of these compounds exhibit regulant activity at very low concentrations, e.g., of about $10^{-10}$ molar and less. Lactic anhyride and higher polylactides form from monomolecular lactic acid at lactic acid concentrations of about 50 percent or greater in water. Both lactic anhydride and polylactides revert to monomolecular lactic acid upon dilution with water to concentrations below 50 percent. The active form of the growth regulant in the plants may be monomolecular L-lactic acid or polylactides of L-lactic acid of varying molecular weight. The polylactides could form on the foliage of treated vegetation (even when monomolecular lactic acid is applied in relatively dilute solutions) upon evaporation of water from the applied solution. The polylactides, if applied as such or formed on the plant foliage, probably hydrolyze within the plant (upon exposure to water) to form monomolecular lactic acid. Similarly, compounds which, in a plant environment, are converted to L-lactic acid or the anhydride or polylactides of L-lactic acid, are also effective for introducing the active growth regulant into treated plants. Whatever the active species actually is, I have found that monomolecular L-lactic acid and the anhydride and higher polylactides of L-lactic acid exhibit growth regulant activity when contacted with plants. Accordingly, when employed to describe the various aspects of this invention, the term L-lactic acid is intended to incorporate the anhydride and higher polylactides of L-lactic acid and compounds which convert to L-lactic acid or its anhydride or polylactides when applied to plants, as well as L-lactic acid itself. Illustrative of compounds which convert to L-lactic acid when applied to plants are salts and esters of both L-lactic acid and polylactic acid, e.g. of polylactides. Illustrative salts include ammonium and metal salts, in particular alkali and alkaline earth metal salts, with the alkali metal salts being particularly preferred. Salts of organic bases are also illustrative, including salts of amines (including quaternary ammonium compounds) phenol and phosphines (including quaternary phosphosinium compounds). Illustrative amines include compounds of the formulae $RNH_2$, $R_2NH$, $R_3N$ and $R_4N^+$. Similarly, illustrative phosphines and phosphosanium compounds are compounds having the empirical formulas $RPH_2$, $R_2PH$, $R_3P$ and $R_4P^+$. In the cases of both the amines and phosphines, the R groups can be any monovalent organic radical, and each amine and/or phosphine can have different organic radicals attached, i.e. the R groups in each amine and/or phosphine can be the same or different monovalent organic radicals. Illustrative organic radicals include those having 1 to about 10, typically 1 to about 4 carbon atoms, and they can contain hetero-atoms such as O, S, N, etc. and pendant functional groups such as hydroxyl, carboxyl, carbonyl, thiol, thiocarbonyl, etc. The most preferred compounds, including the salts and esters discussed hereinafter, are those which have sufficient solubility in water to dissolve in water at ambient temperature (e.g. 20° C.) to the extent of at least 2, and preferably at least 4, most preferably at least 10 ounces of equivalent lactic acid per 100 gallons of water in order to enable effective dosage rates with reasonable spray volumes for application to plants. The same solubility considerations apply to the esters of lactic acid and other compounds which convert to L-lactic acid when applied to plants.

Illustrative esters of L-lactic acid include esters of mono- and/or polyhydric alcohols and thiols. As in the case of the organic basis, the alcohols and thiols generally have 1 to about 10 carbon atoms, preferably 1 to about 4 carbon atoms, and can contain hetero-atoms such as O, S, N, etc., and pendant functional groups, such as hydroxyl, carboxyl, carbonyl, thiol, thiocarbonyl groups etc. Similarly, esters of L-lactic acid with mono- or polybasic organic acids and/or thiol-acids can also be employed. Such acids are, for instance, those formed by reacting the described mono- or polybasic acids or thioacids with the alphahydroxyl group on the L-lactic acid. While any mono- or polybasic acid or thioacid (i.e. esters of such acids and L-lactic acid) can be employed, the acid moiety of such esters will typically have 1 to about 10, preferably 1 to about 4 carbon atoms and can contain hetero-atoms such as O, S, N, etc., and pendant functional groups such as hydroxyl, carboxyl, carbonyl, thiol, and thiolcarbonyl groups, etc.

The useful L-lactic acid and compounds which convert to L-lactic acid can be illustrated by the empirical formula $CH_3 - CH(OY) - CO(OX)$ wherein Y and X are independently selected from hydrogen and monovalent organic radicals, with X also optionally being a monovalent, ionizable, inorganic cation, preferably ammonium or alkyl or alkaline earth metal cation, most preferably ammonium or alkaline metal cation. When Y and/or X are monovalent organic radicals they typically have the characteristics described above for the salts of L-lactic acids with organic basis, e.g. the amines and/or phosphines, (in the case of X) or the described esters of L-lactic acid. Thus, when either X or Y is an organic radical, it will typically have 1 to about 10, preferably 1 to about 4 carbon atoms and may contain the hetero-atoms and/or pendant functional groups described above for the organic basis, alcohols/thiols and organic acids. Of course, in the case of lactic acid per se, both X and Y are H.

The essential aspect of the salts and esters of L-lactic acid, and of the compounds which convert to L-lactic acid in general is that they capable of forming, and do form, lactate anion when applied to plants. Thus, if the salts, esters, etc., hydrolyze in water to form latic anion, or if they do so on the foliage of plants, they are suitable for use in the methods of this invention. This can be readily determined, for instance, in a dilute aqueous solution, such as might be employed for foliar application, by analyzing the solution for lactate anion. If the ester, salt, etc., produces lactate anion in dilute, aqueous solution, it is suitable for use in the methods of this invention. Similarly, sample solutions can be applied to sample plants and the sample plants then analyzed for L-lactic acid and compared to plants of the same population not treated with the solution to determine if the concentration of L-lactic acid in the plants has been increased by such treatment. If an increase of L-lactic acid is seen, the applied compound has been converted to L-lactic acid when applied to the plants, and it is thus also suitable for use in these methods.

As used elsewhere herein, the term "L-lactic acid, or similar nomanclature, is intended to refer either to lactic acid per se or to one or more compounds which convert to L-lactic acid when applied to plants. For instance, the description of lactic acid dosage rates, concentrations, etc. is intended to also include reference to concentrations of such compounds which convert to L-lactic acid on an equivalent lactic acid basis, i.e. the applied concentration of lactic acid precursor will be sufficient to provide the lactic acid dosage rate, concentration, etc. described.

Some of the useful salts and esters are commercially available, and all can be readily prepared by simple chemical reaction. Thus, the salts can be obtained by reacting L-lactic acid with the corresponding base, e.g. sodium hydroxide, ammonium hydroxide, etc., and the esters can be obtained by reacting L-lactic acid with the corresponding alcohol, thiol and/or carboxylic acid under esterification conditions, e.g. in the presence of acid (sulfuric acid, etc.) with mild heating, e.g. refluxing at ambient pressure.

One of the unexpected discoveries in the present invention is that the D-(1)-isomer exhibits little, if any, plant growth stimulant activity, being at least 10 times, and probably at least 100 times, less active than the L-(d)-isomer. Further the D-isomer appears to inhibit or suppress the activity of the L-isomer. Accordingly, the preferred compositions useful in the methods of this invention comprise those in which the L-isomer constitutes at least a major portion of the lactic acid present or generated by ionization or hydrolysis of salts or esters. Usually the L-isomer will comprise at least about 60, preferably at least about 80, and most preferably at least about 90 percent of the lactic acid contained in the composition. Presently, the most preferred compositions are those in which the L-isomer constitutes 80 to 100 percent, and preferably 100 percent of the lactic acid contained in the composition as applied.

The L-isomer or precursor can be applied neat although this procedure is usually undesirable for stimulating plant growth due to the high specific activity of the L-isomer. The L-isomer stimulates plant growth at concentrations as low as $10^{-10}$ molar. Application of the neat material or concentrated solutions also complicates the distribution of the active component to the treated crop. Accordingly, the compositions useful in the methods of this invention usually constitute solutions of the L-isomer in a suitable solvent such as water, lower molecular weight mono- and polyhydric alcohols, ethers, carbon disulfide, and similar solvents. Aqueous solutions of the L-isomer (or precursor) are very active growth regulants and are presently preferred. The L-isomer will usually be present in the applied solution at a concentration of at least $10^{-10}$ molar. Although L-lactic acid remains active in solution at even lower concentrations, it is difficult to apply sufficient amounts of that compound to the treated plants when using solutions of lower concentration due to run-off of the applied solution from the plant foliage. Accordingly, solutions useful in the methods of this invention will usually have equivalent L-lactic acid concentrations within the range of $10^{-10}$ to about 4 molar, normally about $10^{-9}$ to about 2 molar. Dilute solutions within these ranges are usually preferred to stimulate growth and promote fruit production. Thus, when plant stimulation is desired, the L-isomer should be present in the applied solution at a concentration within the range of about $10^{-10}$ to about $10^{-2}$ molar, generally $10^{-9}$ to about $10^{-2}$ molar, and preferably, about $10^{-7}$ to about $10^{-2}$ molar. Solutions containing higher concentrations of the active L-isomer can be employed.

While the described L-lactic acid-containing compositions are active plant growth regulants and thus can be employed in the methods of this invention, they are hydrolytically unstable under certain conditions and are subject to bacterial attack. Bacteria can convert the active L-isomer to inactive species within a relatively short period of time at temperatures as low as 80° F. Thus, while the L-lactic acid solution can be sterilized during its manufacture, there remains a significant risk of bacterial contamination during storage, transportation, mixing, and application.

Accordingly, compositions which are stabilized against hydrolytic decomposition and bacterial attack are presently preferred for use to regulate the growth of plants in accordance with the methods of this invention. These novel compositions comprise lactic acid of which a major portion is the dextrorotatory L-(d)-isomer of lactic acid and a preservative which is sufficient to prevent conversion of the L-isomer to an inactive form by bacterial attack. Suitable preservatives include sufficient acid concentrations to maintain a pH of about 5 or less and/or sterilants which inhibit bacteria growth.

The hydrolytic stability of the L-isomer can be maintained in aqueous solutions by maintaining solution pH within the range of about 3 to about 10, preferably within the range of about 4 to about 8, and most preferably within the range of about 4 to about 6. Lactic acid will react with water at relatively mild temperatures as low as 80° F. under either basic or acid conditions outside the preferred ranges. The rate of hydrolysis is relatively slow at low temperatures e.g., 80° F., and increases rapidly as temperature is increased. The rate of hydrolytic conversion of the L-isomer is also relatively low at pH levels of about 3 and about 10, and increases dramatically as pH drops below 3 or is increased to levels above 10. The rate of hydrolysis can also be reduced by reducing the water concentration in the composition, i.e., increasing the lactic acid concentration. However, the hydrolytic conversion of L-lactic acid can increase dramatically upon dilution of the concentrated acid prior to application if the solution pH is not maintained within the prescribed ranges. Accordingly, the preferred aqueous solutions of this invention contain sufficient acid and/or base to maintain the pH of the solution within the ranges described above. pH buffers are also particularly convenient for this purpose and should have buffer points within the range of about pH 3 to about pH 10, preferably about pH 4 to about pH 6. The buffers also should be nonreactive with the L-lactic acid. Suitable pH buffers include $H_3PO_4\text{-}xH_2PO_4$, citric acid - x-citrate (wherein x connotes a monovalent cation such as sodium, potassium, and ammonium), and other buffer pairs which have buffer points within the prescribed ranges. The ammonium form of the buffer salt is presently preferred since it does not produce insoluble lactates which cause precipitation of the active component from the aqueous solution.

Essentially any acid, including lactic acid, can be employed to maintain a pH of about 5 or less in the compositions of this invention and thereby, minimize the bacterial deactivation of the L-isomer. However, concentrations of lactic acid which are sufficient to maintain pH levels of about 5 or less are often above the concentration desired in the applied solution. Accordingly, the addition of other acids is presently preferred. Illustrative of suitable acids are phosphoric, sulfuric, nitric, hydochloric, and similar acids.

Bacterial decomposition of the L-isomer can also be inhibited, or negated altogether, by any one of various known sterilants, such as the bacteriolytic and bacteriostatic compositions. Illustrative of sterilants that can be employed in the novel compositions of this invention are ethanol, formaldehyde, terramiacan, xylene, toluene, phenylmercuric nitrate, phenylmercuric acetate, copper sulfate, sodium azide, hydrogen peroxide, chlorine, benzisothiozolone, 2[(hydroxy methyl)amis]ethanol, 1-(3-chloroalkyl)-3,5,7-triaza-1-azoneaodamantane chloride, dibromocyanobutane, etc. Sterilant concentrations within the range of about 10 to about 4,000 parts per million (ppm) are usually effective for most applications.

In accordance with the methods of this invention, the plants to be regulated are contacted with a growth regulating amount of the compositions useful in this invention. The L-(d)-lactic acid-containing composition can be applied to the foliage and/or to the roots of the treated plants. The timing of application is relatively important when it is desired to increase the fruit production of fruit-bearing plants. In general, the L-lactic acid component should be applied to the plants during the flowering stage or in the early stages of the fruit-bearing cycle, or both. Ideally, the L-lactic acid component can be applied to the plants at one or more times between the first bud stage and the fruit-set stage, preferably between the first-bud stage and the petal-drop stage for both annual and perennial varieties. Significant increases, e.g., 10 percent and more, in fruit production can be achieved by treatment at essentially any time within these stages of plant development. However, it is presently preferred that at least one application of the L-latic acid component be made within several days of the first-bud stage of development.

Significant improvements in foliage development on non-fruit bearing plants, such as grasses and timber crops, can be accomplished at any time during the growth stage, usually between the spring and fall when the crop is at its active growing cycle.

Significant increases in the growth of non-fruit bearing crops and in the growth and fruit production of fruit-bearing crops can be realized by foliar application of the L-lactic acid component at dosage rates within the range of about 2 to about 100, usually about 4 to about 50, and preferably about 4 to about 25 ounces of equivalent L-lactic acid per acre. The lower dosage rate range of 4 to about 25 ounces per acre is ideally suited to most agricultural row crops and flowering nursery crops. Crops which have a larger abundance of foliage, such as wood crops and some grain and fiber crops such as wheat, corn, and cotton, benefit more by contact with higher dosage within the broader range of about 2 to about 100 ounces per acre of L-lactic acid. Significant growth stimulation can also be achieved by applying the L-lactic acid to the soil in the vicinity of the plant roots. Suitable dosage rates for this mode of application are usually within the range of about 8 to about 400 ounces per acre, preferably about 10 to about 200 ounces per acre of L-lactic acid.

The enhancement in vegetative growth and the increase in fruit production is dose-sensitive to some extent for each crop. As a rule, crops having a greater abundance of vegetative growth, such as cotton and wood crops, should be treated with higher dosage rates of L-lactic acid than are physically smaller plants such as vegetables and tuberous crops which have lesser amounts of vegetative growth.

The concentration and dosage rate of the L-lactic acid component should be correlated to provide adequate spray volume to contact a significant portion of the treated foliage and enable adequate distribution of the applied solutions as a spray with available equipment. Spray volumes in the range of about 5 to about 200 gallons per acre are sufficient to afford adequate coverage and spray distribution for essentially all plant types. Spray volumes of about 5 to about 100 gallons per acre are usually adequate for most agricultural crops, and spray volumes within the range of about 10 to about 60 gallons per acre are presently preferred for the treatment of agricultural row crops and nursery plants. As in the case of dosage rate, the optimum spray volume will vary depending upon crop type, primarily as a function of the amount of vegetative growth presented by the treated plants. Thus, relatively higher spray volumes are better suited for the treatment of larger crops such as cotton, corn and tree crops, while lower spray volumes are better suited for the treatment of vegetables and tuberous plants. When the L-lactic acid is injected into the plant root zone, the volume of L-lactic acid solution injected per acre should be sufficient to afford adequate distribution of the L-lactic acid throughout the root zone of the treated plants. Dosage rates suitable for this purpose will usually be within the range of about 10 to about 400, generally about 20 to about 400, and preferably about 30 to about 300 gallons per acre.

The invention is further described by the following examples of which are illustrative of specific modes of practicing the invention and are not intended as limiting the scope of the invention as defined by the amended claims.

EXAMPLE 1

Separate portions of pure L-(d)-lactic acid were diluted with distilled water to produce five different solutions having concentrations of $10^{-1}$, $10^{-3}$, $10^{-5}$, $10^{-7}$, and $10^{-9}$ molar. Three separate 5 ml. portions of the $10^{-1}$ molar solution were then placed in three separate petri dishes lined with filter paper and each containing approximately 15 garden cress seeds. Three separate 5 ml. portions of the remaining four solutions were also placed in filter paper-lined petri dishes containing approximately 15 garden cress seeds. A sixth series of three petri dishes containing approximately 15 garden cress seeds were treated only with distilled water. The garden cress seeds were germinated in the dark for three days after which each seed root in each petri dish was measured and all root lengths for each series of three replicates were averaged to obtain an average root length for that treatment. The average length of each replicate was then divided by the average length of the control (water only) to yield a root length ratio $L_{test}/L_{control}(L_t/L_c)$. Values below 1 indicate that the root length in the test series was less than that of the control series and that root growth suppression had occurred. Values for the $L_t/L_c$ ratio greater than 1 indicate root growth enhancement.

Figure 1:
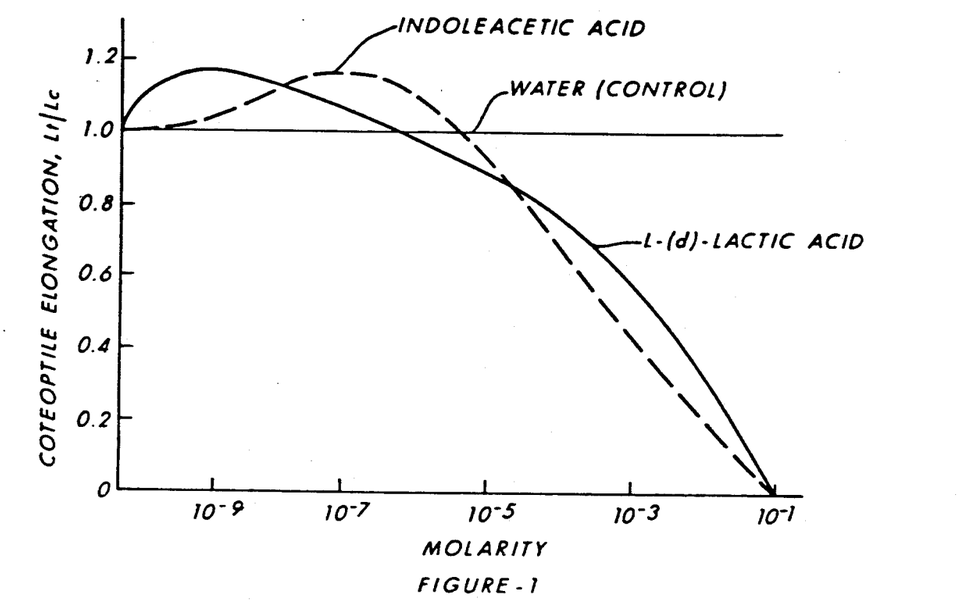
FIG. 1 is a graphic presentation of Cress Test results illustrating the root growth stimulating and inhibiting activity of L-lactic acid and of indoleacetic acid.

These results are presented graphically in FIG. 1 and indicate that the root growth suppression-stimulation promoted by a L-lactic acid solution is characteristic of classical auxin-like activity. Also illustrated graphically in FIG. 1 are data published in the literature for indole acetic acid (IAA), a widely studied plant growth regulant.

Significant root growth stimulation occurred with L-lactic acid at concentrations approximately 2 orders of magnitude below those at which similar responses were induced by indole acetic acid. Thus, L-lactic acid is a much more active plant growth regulant than is indole acetic acid, at least so far as that activity is evidenced by the cress seed root elongation test.

EXAMPLE 2

Figure 2:
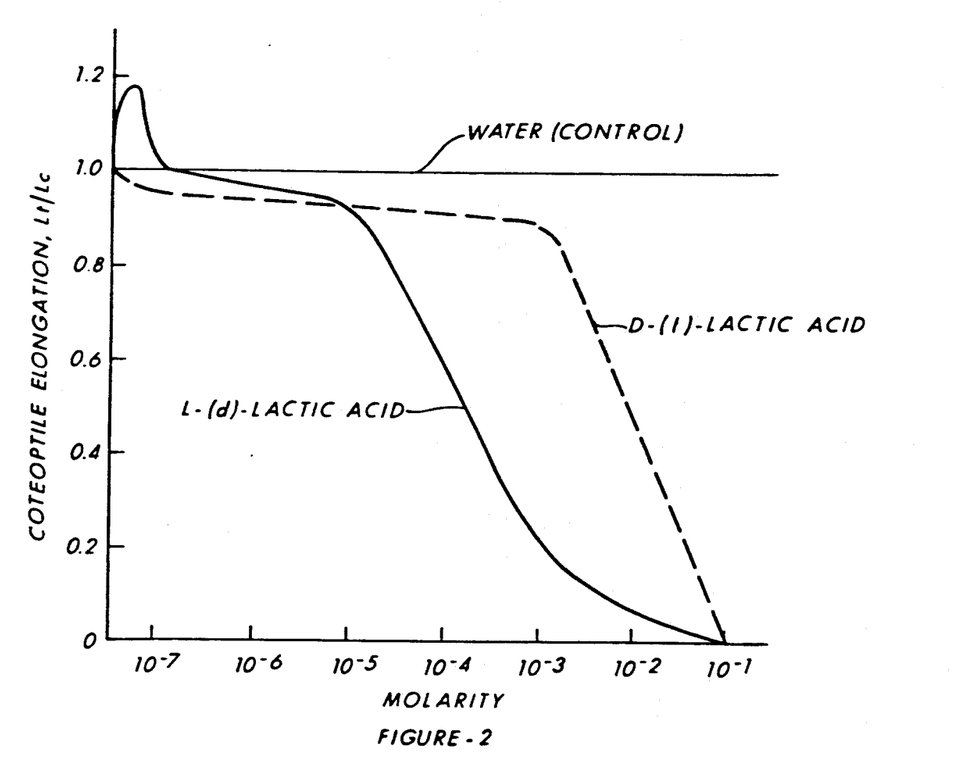
FIG. 2 is a similar graphic presentation of data illustrating the root growth regulating activity of L-lactic acid and of D-(d)-lactic acid.

The garden cress seed root elongation-suppression test described in Example 1 was repeated using three replicates each of four different concentrations of L-lactic acid in distilled water, which concentrations corresponded to $10^{-1}$, $10^{-3}$, $10^{-5}$, and $10^{-7}$ molar. Germinated seed root lengths were measured and averaged as described in Example 1. These results are presented graphically in FIG. 2. The portion of the curve in FIG. 2 which represents the response of the garden cress seed roots to L-lactic acid concentrations below $10^{-7}$ molar is reproduced based on the results of Example 1.

EXAMPLE 3

The garden cress seed root elongation-suppression test described in Example 1 was repeated employing four different concentrations of D-lactic acid (the levorotatory isomer) in distilled water. These concentrations corresponded to $10^{-1}$, $10^{-3}$, $10^{-5}$, and $10^{-7}$ molar. Three separate replicates were tested at each concentration, and root lengths were measured and averaged as described in Example 1. The results are presented graphically in FIG. 2. Comparison of the results of Examples 2 and 3 illustrate that the levorotatory [D-(1)-] isomer of lactic acid has little if any growth regulating activity and that it is a far less active plant growth regulant than the levorotatory isomer. The results of Example 3 also indicate that D-lactic acid has little, if any, tendency to stimulate the growth of germinating seed roots even at relatively low concentrations.

EXAMPLE 4

Yellow flowering variety alfalfa seeds were planted in a sandy loam soil after which 20 ml. of a $10^{-5}$ molar solution of L-lactic acid were applied topically to the soil. Four replicates were treated and these were compared to four replicates of the same seed population planted in the same soil but not treated with the L-lactic acid solution. More seeds germinated in the treated plots than in the untreated (control) plots. All plants were harvested after nine weeks of growth and weighted. The alfalfa treated with L-lactic acid produced 25 weight percent more vegetative growth than the untreated control.

EXAMPLE 5

The operation of Example 4 was repeated with the exception that 50 ml. of the $10^{-5}$ molar L-lactic acid solution was applied to the soil surface after planting of the yellow flowering variety alfalfa seeds. Again more plants survived in the treated plots, and the treated plants produced approximately 25 percent more vegetation growth than the control.

EXAMPLE 6

Approximately equal numbers of yellow flowering variety alfalfa seeds were planted in several pots containing a sandy loam soil. Four series of four pots each were treated with 20 ml. of a $10^{-5}$ molar solution of L-lactic acid in distilled water. The solution was applied to the plants by foliar spraying at emergence (5 days after planting), and three weeks, six weeks, and nine weeks after emergence. The plants were harvested twelve weeks after emergence, weighted, and compared to an untreated control. The test series which were treated five days after planting and three weeks and six weeks after emergence all produced approximately 20 to 25 weight percent more vegetative growth than did the control series. The plants treated nine weeks after emergence did not produce statistically significant amount of vegetative growth above that produced by the untreated control plants.

EXAMPLE 7

The operation of Example 6 was repeated with the exception that 50 ml. of the $10^{-5}$ molar L-lactic acid solution was applied to each test series. As in the case of the 20 ml. treatment, the plants treated 5 days after planting, and two weeks and six weeks after emergence showed approximately 20 to 25 weight percent greater vegetative growth than the control, while the plants treated nine weeks after emergence and harvested twelve weeks after emergence did not evidence a significant gain in vegetative growth over the control. The absence of a statistically significant gain in vegetative growth for the nine week treatment may be due to the relatively short time between treatment and harvest.

EXAMPLE 8

Tiny Tim tomatoes which had already set fruit approximately 0.5 to 1.5 centimeters in diameter were treated with an aqueous solution of L-lactic acid in distilled water having a lactic acid concentration of $10^{-5}$ molar. The solution was applied to the plant foliage at a rate of approximately 4 ml. per plant. No significant increase in fruit size or quantity was obtained in comparison to untreated control plants.

EXAMPLE 9

The operation of Example 8 was repeated with the exception that the L-lactic acid solution had a lactic acid concentration of $10^{-3}$ molar. Again no increase in fruit size or quantity was observed as compared to the untreated controls.

EXAMPLE 10

The operation of Example 8 was repeated with the exception that the tomato plants were treated with two separate foliar applications of approximately 4 ml. each of the $10^{-3}$ molar L-lactic acid solution in distilled water. The first application was made at the full-bloom stage (maximum flowering), and the second application was made two weeks later (after fruit set). The tomatoes were harvested after reaching maturity, and the treated tomatoes were approximately 15 percent larger and matured approximately 50 percent faster than tomatoes on the untreated control plants.

EXAMPLE 11

The operation of Example 10 was repeated with the exception that the L-lactic acid solution had an L-lactic acid concentration of $10^{-5}$ molar. As in the case of the $10^{-3}$ molar solution, the treated plants produced tomatoes approximately 15 percent larger by weight and which matured approximately 50 percent faster than the untreated controls.

EXAMPLE 12

Navel orange trees were treated by foliar application at the first petal-drop stage of five ounces per acre of L-lactic acid in 30 gallons per acre aqueous spray volume. The crop was allowed to set and mature and was harvested and weighed. The untreated control plot produced 820 boxes of navel oranges per acre, while the treated plot produced 1,218 boxes of the oranges per acre.

EXAMPLE 13

Cabernet grapes were treated by foliar application of L-lactic acid at a dosage rate corresponding to 8 ounces of L-lactic acid per acre in 30 gallons per acre spray volume. The application was made at the first berry stage, and the grapes were allowed to mature and were harvested. The yield from the treated grape plants was 15 to 20 percent greater than that of untreated control plants in the same population, and the sugar content of the treated grapes was approximately 2 percentage points higher than in the untreated grapes.

EXAMPLE 14

Sylvaner Riesling grapes were treated by foliar application of L-lactic acid at a rate corresponding to 8 ounces per acre in 30 gallons per acre of spray volume at the first berry stage. The grapes were allowed to mature and were harvested and compared to grapes produced by untreated control plants in the same population. The yield from the treated Riesling grape plants was 15 to 20 percent greater than that of the untreated controls.

EXAMPLE 15

Murietta tomatoes were treated by foliar application of a solution of L-lactic acid at a dosage rate corresponding to 8 ounces of L-lactic acid per acre dissolved in 30 gallons per acre spray volume. The application was made at peak flowering, and the fruit was allowed to set and mature and was harvested and compared to fruit obtained from untreated plants in the same populations. The yield of the treated plants was approximately 30 percent higher than that of the untreated plants.

EXAMPLE 16

Pima cotton was treated by foliar application of an aqueous L-lactic acid solution at a dosage rate corresponding to 16 ounces of L-lactic acid per acre dispersed in 30 gallons per acre of spray volume. The application was made at peak flowering, and the cotton was allowed to mature and was harvested and compared to cotton obtained from untreated, control plants in the same population. The treated plants produced approximately 20 percent more cotton than the untreated plants.

EXAMPLE 17

Valencia oranges were treated by foliar application of 16 ounces per acre of L-lactic acid in 30 gallons per acre of aqueous solution spray. The spray was applied at the first petal-fall stage (peak flowering), and the fruit was allowed to mature and was harvested under normal horticultural conditions. The treated trees produced 1,400 boxes of oranges per acre compared to 800 boxes per acre for untreated control trees in the same population.

EXAMPLE 18

Zinfandel grapes treated by foliar application of 4 ounces per acre of L-lactic acid in 30 gallons per acre of aqueous solution spray volume. The spray was applied at the first berry stage, and the grapes were allowed to mature and were harvested under normal horticultural conditions. The yield of the treated Zinfandel grape plants was 12 percent higher than that of untreated plants in the same population.

EXAMPLE 19

Tiny Tim tomatoes can be treated by foliar application with 4 ml. per plant of a $10^{-3}$ molar solution of ammonium (L) lactate in distilled water at the full-bloom stage (maximum flowering) to increase fruit production.

EXAMPLE 20

The operation described in Example 19 can be repeated substituting sodium (L) lactate for the ammonium lactate employed in Example 19 to increase fruit production.

EXAMPLE 21

The operation described in Example 19 can be repeated by substituting potassium (L) lactate for the ammonium lactate employed in Example 19 to increase fruit production.

EXAMPLE 22

Navel orange trees can be treated to increase fruit production by foliar application at the first petal-drop stage of 7 ounces per acre of ethyl (L) lactate applied in 30 gallons per acre spray volume.

EXAMPLE 23

The operation described in Example 22 can be repeated by substituting 9 ounces per acre of 2-hydroxyethyl (L) lactate for the ethyl lactate employed in Example 22 to increase fruit production.

EXAMPLE 24

Cabernet grapes can be treated to increase fruit production by foliar application of 12 ounces per acre of 2-acetoxy (L) propionic acid per acre applied in 30 gallons per acre spray volume at the first berry stage.

EXAMPLE 25

The productivity of the Cabernet grapes described in Example 24 can be increased by applying to the grapes 12 ounces per acre of 2-ethylhexyl (L) lactate in 30 gallons per acre foliar spray at the first berry stage.

EXAMPLE 26

Sylvaner Riesling grapes can be treated to increase fruit production by foliar application of 20 ounces per acre of 2-acetoxy sodium (L) propionate per acre applied in 30 gallons per acre spray volume at the first berry stage.

While particular embodiments of the invention have been described, it will be understood, of course, that the invention is not limited thereto, since many obvious modifications can be made, and it is intended to include within this invention any such modifications as will fall within the scope of the appended claims.

Having described my invention, I claim:

1. A method for stimulating the productivity of plants, which comprises contacting said plants with a productivity stimulating amount of a composition comprising a compound selected from the group consisting of salts, esters and combinations thereof of lactic acid, wherein the L-isomer constitutes the major portion of said compound.

2. The method defined in claim 1, wherein said compound is water soluble and forms lactate anion when dissolved in water.

3. The method defined in claim 1, wherein said compound has the empirical formula $CH_3$-$CH(OY)$-$CO(OX)$, X is selected from H, an organic or inorganic cation, or a monovalent organic radical, Y is selected from H and monovalent organic radicals, and the L-isomer of said compound constitutes at least about 60 percent of said compound.

4. The method defined in claim 3, wherein said compound consist essentially of said L-isomer.

5. The method defined in claim 3, wherein said L-isoner constitutes at least about 80 percent of said compound.

6. The method defined in claim 3, wherein said organic radicals have 1 to about 10 carbon atoms.

7. The method defined in claim 3, wherein said organic radicals have 1 to about 4 carbon atoms, said compound is soluble in water to the extent of at least 2 ounces per 100 gallons of water at 20° C., and said L-isomer constitutes at least about 80 percent of said compound.

8. The method defined in claim 3, wherein at least one of X and Y is other than hydrogen.

9. The method defined in claim 3, wherein Y is H and X is other than H.

10. The method defined in claim 3, wherein Y is H and X is ammonium or alkali metal cation.

11. The method defined in claim 1, wherein said composition is applied to the ground in the vicinity of the root zone of said plants, either before or after the emergence of said plants from the soil, and said plants are selected from non-fruiting grasses.

12. The method defined in claim 1, wherein said plants are selected from fruit-bearing plants, and to said composition is foliarily applied to said fruit-bearing plants during the fruit-bearing cycle of said plants.

13. A method for stimulating the productivity of the plants, which comprises contacting said plants with a productivity stimulating amount of a composition comprising a compound having the empirical formula $CH_3$-$CH(OH)$-$COOX$, wherein the L-isomer of said compound comprises at least about 60 percent of said compound.

14. The method defined in claim 13, wherein said compound is water soluble.

15. The method defined in claim 13, wherein said compound is water soluble, and said L-isomer constitutes at least about 80 percent of said compound.

16. The method defined in claim 11, wherein said compound consists essentially of said L-isomer.

17. The method defined in claim 13, wherein said L-isomer constitutes at least about 80 percent of said compound, said organic radicals have 1 to about 4 carbon atoms, and said compound is soluble in water to the extent of at least 2 ounces per 100 gallons at 20° C.

18. The method defined in claim 17, wherein X is other than hydrogen.

19. The method defined in claim 13, wherein said L-isomer constitutes at least about 80 percent of said compound, and X is selected from ammonium and alkali metal cations.

20. A method for stimulating the productivity of plants, which comprises introducing into said plants a productivity stimulating amount of a composition comprising a compound having the empirical formula $CH_3$-$CH(OH)$-$CO(OX)$, X is selected from H, monovalent organic and inorganic cations and monovalent organic radicals having 1 to about 10 carbon atoms, said compound is soluble in water to the extent of at least 2 ounces per 100 gallons at 20° C., and the L-isomer of said compound constitutes at least about 80 percent of said compound.

21. The method defined in claim 20, wherein said composition is applied to the ground in the vicinity of the root zone of said plants, either before or after the emergence of said plants, and said plants are selected from non-fruiting grasses.

22. The method defined in claim 20, wherein said plants are selected from fruit-bearing plants, and said composition is foliarily applied to said fruit-bearing plants during the fruit-bearing cycle of said plants.

23. The method defined in claim 20, wherein said plants are selected from the group consisting of grains, grasses, fiber crops, and fruiting plants, and said compound consists essentially of said L-isomer.

* * * * *

UNITED STATES PATENT AND TRADEMARK OFFICE
CERTIFICATE OF CORRECTION

PATENT NO. : 5,059,241

DATED : October 22, 1991

INVENTOR(S) : Donald C. Young

It is certified that error appears in the above-identified patent and that said Letters Patent is hereby corrected as shown below:

ON THE TITLE PAGE

REFERENCES CITED
U.S. Patent Documents
    U.S. Patent 4,265,654, issued May 1981, Takematsu (Cl. 71/86)
    U.S. Patent 4,435,203, issued March 1984, Funaki et al. (Cl. 71/76)
    U.S. Patent 2,535,875, issued December 1950, Stewart (Cl. 71/2.7)
    U.S. Patent 3,172,816, issued March 1965, Swintowsky (Cl. 167/82)
    U.S. Patent 4,813,997, issued March 1989, Kennersley et al. (Cl. 71/66)

Foreign Patent Documents
    157167, Japanese Patent 12/1975
    2200941, German Patent DE 8/1982
    1561475, British Patent (Mandell et al.) 2/1980

Signed and Sealed this

Eighth Day of June, 1993

Attest:

MICHAEL K. KIRK

*Attesting Officer*  Acting Commissioner of Patents and Trademarks